United States Patent [19]

Müllner et al.

[11] Patent Number: 5,043,444

[45] Date of Patent: Aug. 27, 1991

[54] PROCESS FOR THE PREPARATION OF ASYMMETRICALLY SUBSTITUTED UREAS

[75] Inventors: Martin Müllner, Traun; Gerhard Stern, Sonnberg; Markus Rössler, Linz, all of Austria

[73] Assignee: Chemie Linz Gesellschaft m.b.H., Linz, Austria

[21] Appl. No.: 552,695

[22] Filed: Jul. 12, 1990

[30] Foreign Application Priority Data

Jul. 28, 1989 [AT] Austria .................................. 1830/89

[51] Int. Cl.$^5$ .................. C07D 265/30; C07D 207/22; C07C 275/06; C07C 275/24

[52] U.S. Cl. ...................................... 544/169; 548/538; 564/56; 564/57; 564/61

[58] Field of Search ............................ 564/56, 57, 61; 544/169; 548/538

[56] References Cited

U.S. PATENT DOCUMENTS

| | | | |
|---|---|---|---|
| 4,354,040 | 10/1982 | Inoue et al. | 564/67 |
| 4,616,094 | 10/1986 | Bosho et al. | 564/73 |
| 4,931,595 | 6/1990 | Rasshofer | 564/393 |

FOREIGN PATENT DOCUMENTS

| | | |
|---|---|---|
| 0025548A3 | 3/1981 | European Pat. Off. . |
| 0124704A2 | 11/1984 | European Pat. Off. . |
| 1908047 | 9/1970 | Fed. Rep. of Germany . |
| 1768805 | 1/1972 | Fed. Rep. of Germany . |
| 2937331A1 | 4/1981 | Fed. Rep. of Germany . |
| 3636190A1 | 4/1988 | Fed. Rep. of Germany . |
| 1457876 | 11/1974 | United Kingdom . |
| 1433920 | 4/1976 | United Kingdom . |

OTHER PUBLICATIONS

Liebig's Annalen Der Chemie, vol. 364, pp. 129-146 (1909).

*Primary Examiner*—Johann Richter
*Attorney, Agent, or Firm*—Wenderoth, Lind & Ponack

[57] ABSTRACT

Process for the preparation of asymmetrically substituted ureas by reaction of a gaseous mixture of isocyanic acid and ammonia having a temperature of 260° to 600° C. with a primary or secondary amine.

10 Claims, No Drawings

PROCESS FOR THE PREPARATION OF ASYMMETRICALLY SUBSTITUTED UREAS

The present invention relates to a process for the preparation of asymmetrically substituted ureas by reaction of a gaseous mixture of isocyanic acid and ammonia at a temperature of 250 to 600° C. with a primary or secondary amine.

Isocyanic acid is a useful reactive C-1 building block for the synthesis of organic compounds. Inter alia, isocyanic acid can be used for the preparation of asymmetrically substituted ureas by reaction with primary or secondary amines.

Mixtures of isocyanic acid and ammonia are used, inter alia, as the starting material for the synthesis of melamine and are obtained by thermal decomposition of ureas, for example according to EP-A 124,704. However, the isolation of the isocyanic acid from this mixture causes difficulties as ammonium isocyanate, which is very easily isomerized to urea again, is formed on cooling the ammonia/isocyanic acid mixture.

It has now unexpectedly been found that, for the preparation of asymmetrically substituted ureas from isocyanic acid and primary or secondary amines, it is not necessary at all to isolate the isocyanic acid from the gaseous mixture of isocyanic acid and ammonia, on the contrary the isocyanic acid does not react to give ammonium isocyanate in spite of the presence of the ammonia, but reacts with the primary or secondary amine to give an asymmetrically substituted urea which can easily be separated from ammonia.

The invention therefore relates to a process for the preparation of asymmetrically substituted ureas, which is characterized in that a gaseous mixture of isocyanic acid and ammonia at a temperature of 250 to 600° C. is reacted with a primary or secondary amine and the asymmetrically substituted urea is isolated.

In one embodiment of the process according to the invention, the reaction takes place in the gas phase. In this case, a primary or secondary amine is introduced into a gaseous mixture of isocyanic acid and ammonia which has a temperature of 250 to 600° C and the reaction mixture is then cooled, after which the asymmetrically substituted urea condenses and is then isolated.

The gaseous mixture of isocyanic acid and ammonia has a temperature of 250 to 600° C., preferably 300 to 450° C., particularly preferably 320 to 380° C.

Primary or secondary amines are to be understood as meaning those compounds which have one or more amino groups. They may optionally be substituted by other groups which are inert under the reaction conditions. Examples of these are identically or differently substituted aliphatic, cycloaliphatic or cyclic amines, such as methylamine, ethylamine, propylamine, hexylamine, dodecylamine, hexadecylamine, isopropylamine, isobutylamine, isooctylamine, tert.butylamine, methylethylamine, ethylbutylamine, cyclohexylamine or dimethylamine, diethylamine, diisopropylamine, diisobutylamine, pyrrolidine, pyrrole, piperidine, morpholine., ethylenediamine, hexamethylenediamine, 4,4'-diaminodicyclohexylmethane or identically or differently substituted aromatic amines, such as aniline, nitroanilines, chloroanilines, tolylamines, benzylamine, dibenzylamine, naphthylamines, phenylenediamines, toluylenediamines and 4,4'-diaminodiphenylmethane.

The primary or secondary amine can be introduced in the gaseous state, if desired with the aid of a carrier gas, or as a liquid by spraying in or dripping in, the amine in this case initially being converted directly into the gaseous state in the reaction mixture owing to its high temperature. It is possible in this case to add the amine to isocyanic acid in approximately equimolar amounts, or to employ an excess of the amine. Preferably, 1 to 7 equivalents, particularly preferably 1.1 to 3 equivalents of amine, are employed per mol of isocyanic acid.

The gas mixture may in this case be diluted with a carrier gas. The carrier gas can be a gas which is inert under the reaction conditions, such as nitrogen, argon or ammonia, or the primary or secondary amine optionally added as a gas can additionally be used as the carrier gas.

The contact time of the reactants is in this case dependent on the size of the apparatus and the flow rate of the gas, a contact time of a few seconds generally being sufficient.

The hot gaseous reaction mixture is then cooled, the asymmetrically substituted urea depositing as a precipitate. However, it is also possible to bring the hot gaseous reaction mixture into contact with an inert diluent by passing it in, or via packed columns, scrubbers and the like. The urea formed in this case condenses in the inert diluent.

In another embodiment of the process, the primary or secondary amine is used in the liquid or molten state or diluted in a diluent which is inert under the reaction conditions. Suitable primary or secondary amines are the abovementioned primary or secondary amines. The gaseous mixture of isocyanic acid and ammonia, which has a temperature cf 250 to 100 ° C, is induced into the primary or secondary liquid molten or diluted amine, it being possible to use an inert carrier gas such as those described above. It is also possible for the amine itself to be used as the diluent and as a result of this to be present in a high excess or to use the amine in a diluent which is inert under the reaction conditions whereby 1 to 7 moles preferably 1 to 3 moles of amine being used per mole of isocyanic acid. It has unexpectedly come to light here that even with a high excess of the amine virtually no symmetrically substituted urea is formed. The temperature cf the vessel is below the boiling point of the amine and the diluent preferably between room temperature and 100 ° C. If desired, cooling of the liquid or molten or diluted amine can also be carried out here in a customary manner, for example with the aid of heat exchangers. If a molten amine is used, the cooling must not lead to the amine crystallizing out again.

For both embodiments of the process according to the invention, suitable inert diluents are water or organic diluents, for example lower aliphatic alcohols, such as methanol, ethanol, isopropanol, aliphatic hydrocarbons, such as pentane, hexane, heptane, aromatic hydrocarbons, such as benzene, toluene, xylene, halogenated aliphatic hydrocarbons, such as methylene chloride, chloroform, carbon tetrachloride, ethyl chloride, ethylene chloride, halogenated aromatic hydrocarbons, such as chlorobenzene, trichlorobenzene, ethers, such as diethyl ether, diisopropyl ether, dibutyl ether, ethyl methyl ether, dioxane, carboxamides, such as dimethylformamide, N-methylpyrrolidone or mixtures of abovementioned diluents.

According to both embodiments of the process according to the invention, the urea formed is accordingly present, depending on the nature of the diluent used or depending on the nature of the urea and depending on the manner of the embodiment, as a solid or dissolved or suspended in the inert diluent used or in the amine used.

The ammonia formed in the reaction escapes and is led off in a customary manner. If desired, dissolved ammonia can, for example, be driven off with the aid of an inert gas, such as, for example, nitrogen or argon.

The process can be carried out continuously or batchwise, but is preferably carried out continuously.

In the manner described above, a solution or suspension of an asymmetrically substituted urea is obtained, or the asymmetrically substituted urea is obtained in solid form. The isolation of the dissolved or solid urea can be carried out in a customary manner, such as, for example, by filtration, evaporating the solvent or dissolving out or scraping off the solid, it being possible, if desired, to carry out a purification of the residue by customary methods, such as distillation, recrystallization or chromatography.

The process yields asymmetrically substituted ureas in good yields and good purity and thus represents an enrichment of the art.

EXAMPLE 1

125 g of urea per hour were continuously introduced into a decomposer. The pyrolysis gases were caused to react with 65 g of methylamine per hour in a heatable tube at 380° C.

The reaction gases were rapidly cooled to room temperature in a scrubber which was operated with water. Altogether, 750 g of urea (12.5 mol) and 389 g of methylamine (12.5 mol) were introduced.

The scrub solution was evaporated to dryness in vacuo and the residue was recrystallized from ethanol. 426 g, i.e. 46% of theory, of methylurea having a melting point of 100° C were obtained in this way.

EXAMPLE 2

As described in Example 1, but using 604 g of methylamine (19.4 mol) methylurea having a melting point of 100° C. was obtained in a yield of 45% of theory.

EXAMPLE 3

As described in Example 1, but using 1164 g of methylamine (37.5 mol), methylurea having a melting point of 100° C. was obtained in a yield of 45% of theory.

EXAMPLE 4

As described in Example 1, but using 250 g of urea (4.2 mol) and 273 g of propylamine (4.6 mol) and using N-methylpyrrolidone as the diluent, propylurea was obtained in a yield of 37% of theory after recrystallizing from diisopropyl ether.

C-H-N analysis:
theoretical: C 46.7%, H 9.8%, N 27.2%
found: C 46.4%, H 9.5%, N 27.3%

EXAMPLE 5

As described in Example 4, but using 547 g of hexylamine (5.4 mol), hexylurea was obtained in a yield of 74% of theory after recrystallizing from water.

C-H-N analysis:
theoretical: C 58.3%, H 11.2%, N 19.4%
found: C 58.5%, H 10.9%, N 19.3%

EXAMPLE 5

250 g of urea were continuously introduced into a decomposer in the course of 2 hours. The pyrolysis gases were introduced into a melt of 1200 g of dodecylamine at a temperature of 80 to 90° C. After completion of the reaction, the excess dodecylamine was distilled off in vacuo and the residue was recrystallized from chloroform. 598.9 g, i.e. 63% of theory, of dodecylurea having a melting point of 105 to 107° C were obtained in this way.

EXAMPLE 7

As described in Example 4, but using 459 g of ethylbutylamine (4.6 mol) and chlorobenzene as the diluent, N,N-ethylbutylurea was obtained in a yield of 62% of theory after recrystallizing from n-hexane. $^1$H-NMR: 0.89 (t,J=7.2 Hz, CH: (butyl); 1.02 (t,J=7.0 Hz, CH$_3$ (ethyl), 1.19-1.47 (m, —CH$_z$—CH$_2$ (butyl)); 3.08-3.20 (m, —CH$_2$—N—C=O); 5.78 (s, —NH$_2$).

EXAMPLE 8

125 g of urea per hour were continuously introduced into a decomposer. The pyrolysis gases were caused to react with 120 g of gaseous dimethylamine per hour in a heatable tube at 380° C. The reaction gases were rapidly cooled to room temperature in a scrubber using water. Altogether, 146 g (2.4 mol) of urea and 160 g (3.6 mol) of dimethylamine were introduced.

The scrubbed solution was evaporated to dryness in vacuo and the residue was recrystallized from ethanol. 117 g, i.e. 55% of theory, of diethylurea having a melting point of 178 -184° C. were obtained in this way.

EXAMPLE 9

As described in Example 4, but using 365.3 g of diethylamine (5.0 mol) and using n-hexane as the diluent, diethylurea having a melting point of 68 -70° C. was obtained in a yield of 30% of theory after recrystallizing from diisopropyl ether.

EXAMPLE 10

As described in Example 4, but using 368.9 g of isopropylamine (6.2 mol), isopropylurea having a melting point of 157-159° C. was obtained in a yield of 39% of theory after recrystallizing from water.

EXAMPLE 11

As described in Example 10, but using ethanol as the diluent, isopropylurea having a melting point of 157-159° C. was obtained in a yield of 45% of theory after recrystallizing from water. EXAMPLE 12

As described in Example 4, but using 426.2 g of isobutylurea (5.8 mol) and toluene as the diluent, isobutylurea was obtained in a yield of 70% of theory after recrystallizing from diisopropyl ether. $^1$H-NMR 0.84 (d,J=7.3 Hz, CH$_3$); 1.55-1.69 (m, CH); 2.80 (t,J=6.3 Hz, CH$_2$—N); 5.41 (s, —NH$_2$); 6.0 (s, broad, —NH—).

EXAMPLE 13

As described in Example 12, but using 426.2 g of tertiary butylamine (5.8 mol) and N-methylpyrrolidone as the solvent, tert. butylurea having a melting point of 177° C. (dec.) was obtained in a yield of 55% of theory after recrystallizing from water.

EXAMPLE 14

As described in Example 4, but using 391.2 g of cyclohexylamine (4.2 mol) and isopropanol as the diluent, cyclohexylurea having a melting point of 196-197° C.

was obtained in a yield of 48% of theory after recrystallizing from methanol.

EXAMPLE 15

100 g of urea per hour were continuously introduced into a decomposer. The pyrolysis gases were caused to react with 250 g of gaseous diisopropylamine per hour in a heatable tube at 320° C. The reaction gases were rapidly cooled in a scrubber using chloroform.

Altogether, 250 g (4.2 mol) of urea and 635 g (6.3 mol) of diisopropylamine were introduced. 370 g of N,N-diisopropylurea, i.e. 60% of theory, having a melting point of 98 101° C. were obtained in this way after recrystallizing from water.

EXAMPLE 16

As described in Example 4, but using 640.6 g of di-isobutylamine (5.0 mol) and N-methylpyrrolidone as the diluent, N.N-diisobutylurea having a melting point of 3–75° C. was obtained in a yield of 30% of theory after recrystallizing from n-hexane.

EXAMPLE 17

As described in Example 6, but using 1400 g of aniline instead of dodecylamine at a temperature of 80 - g0 ° C,phenylurea having a melting point of I45 - 147 ° C was obtained in a yield of 41% of theory.

EXAMPLE 18

As described in Example 6, but using 1300 g of benzylamine instead of dodecylamine at a temperature of 80–90° C., benzylurea was obtained in a yield of 71% of theory after recrystallizing from water.

C-H-N analysis:
theoretical: C 64-0%, H 6.7%, N 18.6%.
found: C 64.0%, H 6.7%, N 18.7%

EXAMPLE 19

As described in Example 6, but using a 20strength solution of dibenzylamine in N-methylpyrrolidone instead of dodecylamine at a temperature of 70 C, N,N dibenzylurea was obtained in a yield of 62% of theory after recrystallizing from water/acetone.

C-H-N analysis:
theoretical: C 75.0%, H 6.7%, N 11.7%.
found: C 74.8%, H 6.7%, N 11.6%.

EXAMPLE 20

As described in Example 6, but using a 20% strength aqueous solution of morpholine instead of dodecylamine at a temperature of 80° C. morpholine-4-carboxamide obtained in yield of 71% of theory after recrystallizing from ethanol. $^1$H-NMR: 3.29 (t,J=4.7 Hz, N-CH$_2$); 3.57 (t,J=4.7 Hz, —O—CH$_2$); 6.16 (O=C—NH$_2$). $^{13}$C-NMR 47.9 (—N—CH$_2$—); 70.0 (—O—CH$_2$—); 162.5 (C=0)

EXAMPLE 21

As described in Example 20, but using a20% strength ethanolic solution of morpholine instead of an aqueous solution at a temperature of 25° C., morpholine-carboxamide was obtained in a yield of 53% of theory.

$^1$H-NMR: 3.29 (t,J=4.7 Hz, N-CH$_2$); 3.57 (t,J=4.7 Hz, —O—CH$_2$); 6.16 (O=C-NH$_2$).

$^{13}$C-NMR 47.9 (—N—CH$_2$—); 70.0 (—O—CH$_2$—), 162.5 (C=O)

EXAMPLE 22

As described in Example 6, but using 1300 g of morpholine instead of dodecylamine at a temperature of 50° C., morpholine—4—carboxamide was obtained in a yield of 53% of theory after recrystallizing from ethanol. $^1$H-NMR: 3.29 (t,J=4.7 Hz, N—CH$_2$); 3.57 (t,J=4.7 Hz, —O—CH$_2$); 6.16 (O=C—NH$_2$).

$^{13}$C—NMR: 47.9 (—N—CH$_2$—); 70.0 (—0—CH$_2$—); 162.5 (C=O)

EXAMPLE 23

As described in Example 6, but using a 20% strength solution of pyrrolidine in dioxane instead of dodecylamine at a temperature of 25° C., pyrrolidine-N-carboxamide was obtained in a yield of 55% of theory after recrystallizing from water.

C-H-N analysis:
theoretical: C 52.6%, H 8.8%, N 24.5%.
found: C 52.4%, H 8.7%, N 24.6%.

EXAMPLE 24

As described in Example 1, but using 300 g of ethylenediamine (5.0 mol), ethylenediurea was obtained in a yield of 40% of theory after recrystallizing from water.

C-H-N analysis:
theoretical: C 32.9%,. H 6.9%, N 38.3% .
found: C 32.8%, H 6.9%, N 38.2%

What we claim is:

1. Process for the preparation of asymmetrically substituted ureas, comprising reacting a gaseous mixture of isocyanic acid and ammonia at a temperature of 250 to 600° C. with a primary or secondary amine and isolating the asymmetrically substituted urea.

2. Process according to claim 1, comprising introducing a primary or secondary amine into a gaseous mixture of isocyanic acid and ammonia at a temperature of 250 to 600° C. and then cooling the gaseous reaction mixture, after which the asymmetrically substituted urea is condensed and isolated.

3. Process according to claim 1 or 2, comprising introducing the primary or secondary amine at a temperature of 320 to 380° C. l;

4. Process according to claim 1 comprising introducing 1 to 7 equivalents of primary or secondary amine per mol of isocyanic acid.

5. Process according to claim 1, comprising introducing 1.1 to 3 equivalents of primary or secondary amine per mol of isocyanic acid.

6. Process according to claim 1, comprising cooling the reaction mixture in an inert diluent.

7. Process according to claim 1, comprising introducing a gaseous mixture of isocyanic acid and ammonia at a temperature of 250 to 600° C. into a primary or secondary amine in liquid or molten state or diluted in a diluent which is inert under the reaction conditions, after which the asymmetrically substituted urea is isolated from the reaction mixture.

8. Process according to claim 7,comprising introducing
   the primary or secondary amine dissolved in a diluent which is inert under the reaction conditions.

9. Process according to claim 1, comprising employing an organic diluent as the inert diluent.

10. Process according to claim 1, comprising employing water as the inert diluent.

* * * * *